United States Patent [19]

Huber et al.

[11] 4,443,105
[45] Apr. 17, 1984

[54] DEVICE USEFUL FOR FLAMELESS ATOMIC ABSORPTION SPECTROSCOPY

[75] Inventors: Bernhard Huber, Uberlingen; Rolf Tamm, Salem; Toma Tomoff, Uberlingen, all of Fed. Rep. of Germany

[73] Assignee: Bodenseewerk Perkin-Elmer & Co., GmbH, Uberlingen, Fed. Rep. of Germany

[21] Appl. No.: 310,190

[22] Filed: Oct. 9, 1981

[30] Foreign Application Priority Data

Nov. 27, 1980 [DE] Fed. Rep. of Germany ....... 3044627

[51] Int. Cl.³ .......................................... G01N 21/74
[52] U.S. Cl. .................................... 356/312; 356/244
[58] Field of Search ................ 356/36, 312, 317, 318, 356/246, 244

[56] References Cited

U.S. PATENT DOCUMENTS

| | | | |
|---|---|---|---|
| 2,983,184 | 5/1961 | Ferrari, Jr. | 356/246 |
| 3,895,873 | 7/1975 | Dennison et al. | 356/312 |
| 4,098,554 | 7/1978 | Huber et al. | 356/312 |
| 4,111,553 | 9/1978 | Garnys | 356/312 X |
| 4,146,331 | 3/1979 | Huber | 356/312 X |

OTHER PUBLICATIONS

L'vov, "Atomic Absorption Determination of Phosphorus by Means of an HGA Atomizer on Introducing Samples into the Furnace on a Probe,38 *Zh. anal. khim.*, vol. 33, #8, pp. 1572-1575, 1978.

Herz, "Thermocouple-Controlled Temperature Programmer for Flash Desorption Spectroscopy," J. Phys. E. Sci. Instrum., vol. 12, 1979.

*Primary Examiner*—F. L. Evans
*Assistant Examiner*—L. A. Dietert
*Attorney, Agent, or Firm*—F. L. Masselle; E. T. Grimes; R. A. Hays

[57] ABSTRACT

An apparatus useful for flameless atomic absorption spectroscopy includes a sample carrier adapted for receiving non-gaseous sample material and means for radiantly heating the sample carrier to effect the uniform thermal decomposition thereof.

11 Claims, 7 Drawing Figures

DEVICE USEFUL FOR FLAMELESS ATOMIC ABSORPTION SPECTROSCOPY

BACKGROUND OF THE INVENTION

The present invention generally relates to an apparatus useful in flameless atomic absorption spectroscopy and, in particular, relates to such an apparatus including means for the radiant heating of a sample.

In a prior art apparatus, for example, an apparatus as described in U.S. patent application ser. no. 239,934, filed on Mar. 3, 1981, a wire helix of temperature-resistant, electrically conducting material, such as tungsten, serves as a sample carrier. In use, a liquid sample is applied to the sample carrier. The sample carrier is provided with electric connections whereby it can be heated in a controlled manner by passing an electric current therethrough. Thus, the liquid sample can be dried and thermally decomposed external to the graphite tube by heating the sample carrier. The "heating device" includes the sample carrier itself acting as a resistor in combination with the electrical connections and the power source.

The known arrangement does, however, have some drawbacks. For example, only relatively small liquid sample quantities can be applied to the wire helix. In addition, the use of solid or powdery samples is not possible.

Furthermore, the sample is essentially heated in a non-uniform way; that is, heating first at the physical contact interface of the sample liquid and wire helix. Thus, the risk of sputtering of sample liquid is always present. Furthermore, the useful life of the heated wire helix is reduced because carbide formation occurs at the surface thereof.

In the prior art, a sample is occasionally introduced into a graphite crucible and inserted into a graphite tube wherein it is heated. Such heating is arranged to be independent of the graphite tube. The independent heating of the crucible inside the graphite tube entails all of the disadvantages mentioned in the above referenced U.S. patent application, which application is incorporated herein.

SUMMARY OF THE INVENTION

Accordingly, it is one object of the present invention to provide an apparatus which enables the handling of relatively large solid or liquid sample quantities, including powdery materials.

This object is achieved, at least in part, by an apparatus comprising a sample carrier that is lamella- or crucible-like and a means for radiantly heating the carrier external to a graphite tube.

Other objects and advantages will become apparent from the ensuing specification and the accompanying drawing.

BRIEF DESCRIPTION OF THE DRAWING

The drawing, not drawn to scale, comprises the following.

DETAILED DESCRIPTION OF THE INVENTION

Figure 1:
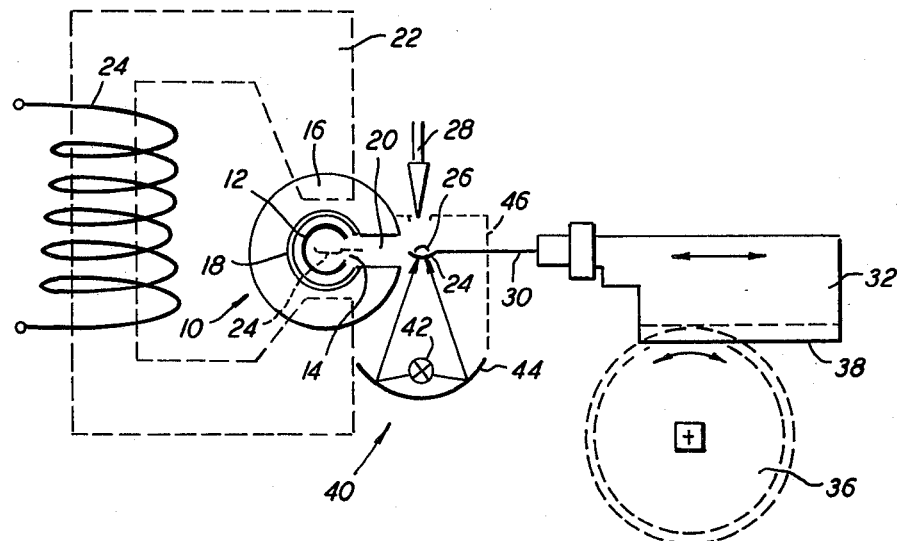
FIG. 1, which is a schematic view of a graphite tube embodying the principles of the present invention.
Figure 2:
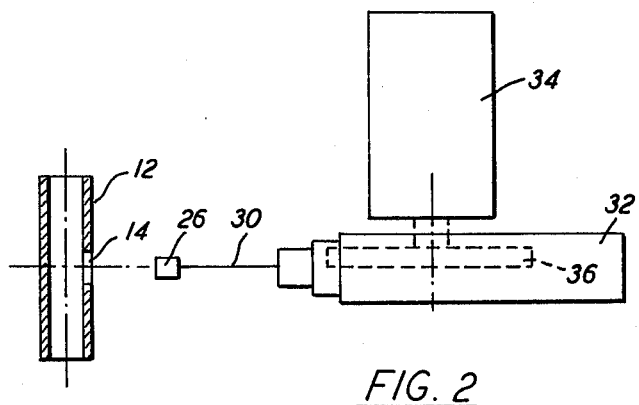
FIG. 2, which is a plane view of the graphite tube of FIG. 1.

In FIG. 1, a graphite tube atomizer or furnace, generally designated by the numeral 10, includes a graphite tube 12, retained in conventional manner between two annular electrodes (not shown), arranged to be heated to high temperatures by an electrical current passed therethrough. The graphite tube 12 has a lateral sample introduction aperture 14 which is surrounded by an insulating jacket 16 having a protective jacket 18 on the inside thereof. The insulating jacket 16 has an aperture 20 therein which is aligned with the sample introduction aperture 14 of the graphite tube 12.

A measuring light beam of an atomic absorption spectrometer passes longitudinally through the graphite tube 12 and through apertures in the annular electrodes. A sample inserted therein is atomized by heating the graphite tube 12, to form a "cloud of atoms" therein. The "cloud of atoms" thus includes atoms of the sample material in this atomic state. In operation, the measuring light beam formed by the spectra lines of a sought sample element are attenuated proportionally to the quantity of the sought element in the cloud of atoms. The concentration of the sought element in the sample can then be derived from this signal.

The above-described graphite tube atomizer 10 is often arranged in the air-gap of coil 24 of a strong electric magnet 22 which can be energized by passing alternating current therethrough. Because of the Zeeman effect, the alternating magnetic field generated thereby causes a periodic change of the wavelength absorbed by the atoms of the sought element. Thereby, the influence of nonspecific background radiation can be eliminated.

A sample carrier 25, which is preferably either a lamella or a crucible, is used to introduce the sample into the graphite tube 12. Preferably, the sample carrier 25 is made of graphite and configured to accept substantially all non-gaseous sample material, including solids and powders. The sample 26 can be applied to the sample carrier 25 by means known in the art, for example, by use of a pipette 28.

The sample carrier 25 is preferably affixed to a carriage 32 by an elongated holder 30. Preferably, the carriage 32 is guided along a straight path longitudinally of the holder 30 by means of a drive motor 34. The drive motor 34 is preferably coupled with the carriage 32 by means of a pinion 36 and a rack 38. The carriage 32 with the holder 30 and the sample carrier 25 can be moved controllably by the drive motor 34 towards the introduction aperture 14 of the graphite tube 12. In a first position of the carriage 32 illustrated in FIG. 1, the sample carrier 25 is in the area of a heating device 40, adapted to radiantly heat the sample carrier 25. In a second position into which the carriage 32 can be moved, illustrated by dashed lines in FIG. 1, the holder 30 with the sample carrier 25 affixed thereto extends through the introduction aperture 14 into the graphite tube 12.

The heating device 40 can, for example, be an inductive heating means or any other known means for imparting radiant thermal energy. In the described preferred embodiment, the heating device 40 is a light source 42 having a reflecting optical element 44 for concentrating the radiation of the light source 42 onto the sample carrier 25. The light source 42 can be, for example, a high intensity halogen lamp. Such a light source heats the sample carrier 25 with the sample 26 therein in a concentrated way without causing any substantial heating of the holder 30 or the like. Hence, the sample is heated "smoothly", that is, quickly but without sputtering.

During the period of drying and thermal decomposition of the sample 26, the sample carrier 25 is positioned in front of the graphite tube 12 in a housing portion 46, into which an inert gas is introduced in order to prevent the graphite sample carrier 25 from burning.

Figure 3:
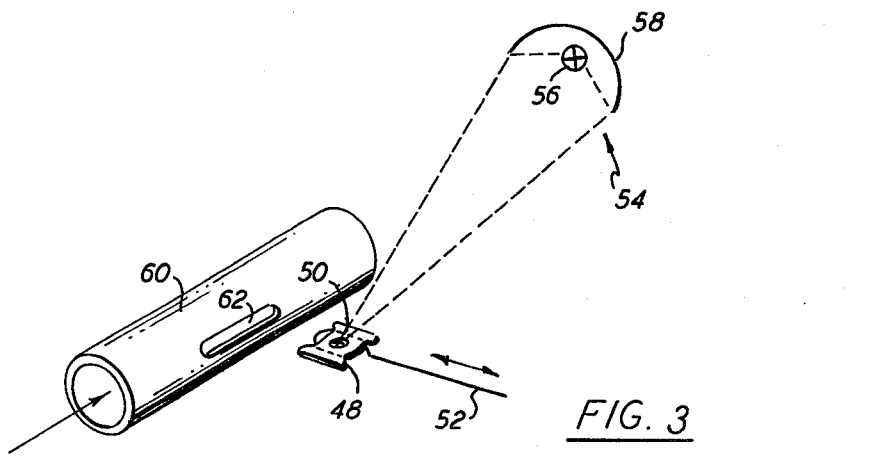
FIG. 3, which is a schematic of a sample carrier embodying the principles of the present invention.

In one embodiment, shown specifically in FIG. 3, the sample carrier 48 is a lamella to which the sample 50 is applied. The lamella is fixed to a holder 52, which in this embodiment is in the form of a tungsten wire. Preferably, the tungsten wire is bent to a U-shape at its front end and snaps into the lamella.

The sample 50 is heated by a heating device 54, i.e. in this embodiment, a light source 56 and a reflector 58 for concentrating the light beam directly onto the sample 50.

As shown, the graphite tube 60 is adapted to include a longitudinal slot 62 for introducing the lamella-like sample carrier 48.

Figures 4, 5:
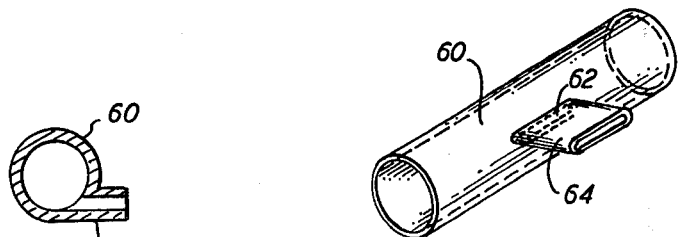
FIG. 4, which is a perspective view of a modified embodiment of the graphite tube of FIG. 3.
FIG. 5, which is a cross-sectional view of another modified embodiment of the graphite tube.

As illustrated in FIGS. 4 and 5, the slot 62 can be surrounded by a collar 64 extending along its edge. The longitudinal sides of the collar 64 may extend substantially perpendicularly from the surface of the graphite tube 60, as illustrated at FIG. 4. Alternatively, the longitudinal sides of the collar 64 may extend substantially tangentially from the surface of the graphite tube 60, as illustrated in FIG. 5.

The collar 64 prevents the graphite tube 60 from being overheated in the median area, as could occur with the graphite tube as depicted in FIG. 3. Furthermore, such a collar 64 prevents part of the cloud of atoms from escaping through the slot 62, which, of course, would result in reduced sensitivity.

Figure 6:
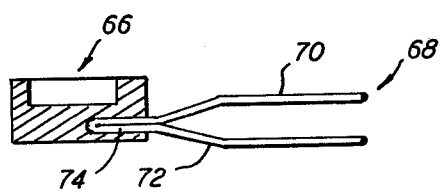
FIG. 6, which is a preferred embodiment of a sample carrier.

The sample carrier 66 depicted in FIG. 6, includes a holder 68 designed to additionally serve as a temperature sensor. To this end, the holder 68 consists of two wires 70, 72 of different materials. The wires, 70 and 72, are joined, for example, by a solder joint 74, in the area of the sample carrier 66 and thus act as a thermocouple. In one instance, the wire 70 is the negative leg and the wire 72 is the positive leg of the thermocouple.

As compared with the usual pyrometric measurement measuring the temperature with a thermocouple offers the advantage that the measurement is not disturbed by the radiation of the light source 42 or 56.

Figure 7:
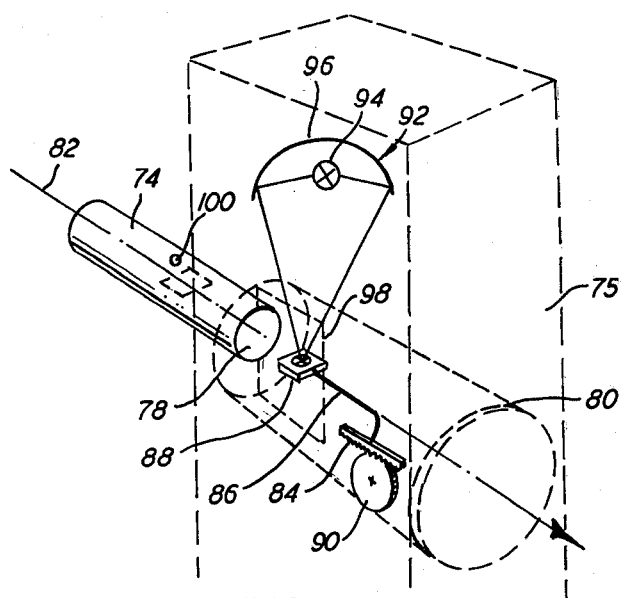
FIG. 7, which is a schematic view of still another apparatus embodying the principles of the present invention.

As illustrated in FIG. 7, the graphite tube 74 is retained between cooling chambers 76 of which only one is shown. Each of the cooling chambers 76 includes an aperture 80 aligned with the longitudinal bore 78 of the graphite tube 74 to permit passage therethrough of the measuring beam 82. A carriage 84 (similar to carriage 32) with a holder 86 and a sample carrier 88 is arranged in the aperture 80 of one of the cooling chambers 76 below the path of rays of the measuring beam 82 and is movably guided longitudinally to the aperture 80 and the graphite tube 74. A drive motor 90 imparts the desired motion. A heating device 92, again formed, for example, by a light source 94 and a reflector 96 for radiantly heating the sample carrier 88 is also arranged in the cooling chamber 76. A charging window 98, through which the sample carrier 88 is accessible and through which vapors can emerge during the period of drying and thermal decomposition of the sample, is provided in the cooling chamber 76 in the area of the heating device 92.

The drive motor 90 and the carriage 84 are controlled in a similar way as with the embodiment shown in FIG. 1. The sample carrier 88 can take the first position in the area of the heating device 92 in front of the graphite tube 75, illustrated in FIG. 7 by solid lines. The second position of the carrier 88 is inside the graphite tube, illustrated by dashed lines in FIG. 7.

This arrangement offers the advantage that conventional graphite tubes can be employed herewith. It is possible to charge the graphite tube 74 optionally in conventional manner, that means directly through a small introduction aperture 100, or by means of the sample carrier 88 described.

The holder 86 may consist of high-melting metal, such as graphite or glassy carbon or the like. If the holder 86 serves as a temperature sensor the variation in the resistance of the connecting wires can be a measure of the temperature as well.

For the purpose of illumination, the light source may be adapted for being switched to reduced brightness. Thus, it can be well observed where on the carrier the sample is dispensed. For manual pipetting, this is often quite necessary. The lamp can be energized by a lower voltage than during the drying period, such that the sample carrier is illuminated. The following drying period with the associated carrier temperature can be established by observing the drying effect. This effect can be observed very well on the illuminated sample carrier.

Although specific embodiments have been described herein, such embodiments are considered exemplary and not limiting. The present invention is defined only by the appended claims and the reasonable interpretation thereof.

What is claimed is:

1. Apparatus useful for flameless atomic absorption spectroscopy; said apparatus comprising:
   a sample carrier adapted to be inserted into a graphite tube and being configured to accept non-gaseous sample material;
   means, external to said graphite tube, for radiantly heating said sample carrier;
   an elongated sample carrier holder, said sample carrier being supported by one end of said sample carrier holder, said holder being a temperature sensor;
   a carriage, said carriage having the other end of said holder secured thereto, said carriage being guided along a straight path longitudinally of said holder and being moveable between a first position, whereat said sample carrier is in the area of said heating means, and a second position, whereat said holder with said sample carrier extends into the interior of said graphite tube through said aperture; and
   a drive motor coupled to said carriage, said carriage, with said holder and said sample carrier, being arranged to be controllably moved by said motor toward an introduction aperture of said graphite tube.

2. Apparatus as claimed in claim 1 wherein said heating means includes a light source and an optical element for concentrating the radiation from said light source onto said sample carrier.

3. Apparatus as claimed in claim 2 wherein said light source is adapted to be switched to reduced brightness for illumination purposes.

4. Apparatus as claimed in claim 1 wherein said sample carrier is formed of graphite.

5. Apparatus as claimed in claim 1 wherein:
said graphite tube is retained between cooling chambers, each of which includes an aperture aligned with the longitudinal bore of said graphite tube;
said carriage with said holder and said sample carrier being arranged in one of said cooling chambers below the path of rays of the measuring beam and is guided for movement longitudinally of said graphite tube; and
said means for heating said sample carrier is arranged in said cooling chamber.

6. Apparatus as claimed in claim 5 wherein a charging window is provided in said cooling chamber through which charging window said sample carrier is accessible and through which vapors can emerge during the drying and decomposing of the non-gaseous sample.

7. Apparatus as claimed in claim 1 wherein said holder includes two wires of different material joined by a soldered joint in the area of sample carrier and which so act as a thermocouple.

8. Apparatus as claimed in claim 1 wherein said graphite tube has a longitudinally extending slot on its median area for introducing said sample carrier.

9. Apparatus as claimed in claim 8 wherein said slot is surrounded by a collar extending along its edge.

10. Apparatus as claimed in claim 9 wherein said longitudinal sides of said collar extend substantially perpendicularly from said graphite tube.

11. Apparatus as claimed in claim 9 wherein said longitudinal sides of said collar extend substantially tangentially from said graphite tube.

* * * * *